United States Patent [19]

Durden et al.

[11] 3,954,998

[45] May 4, 1976

[54] SUBSTITUTED PHENYL INDANDIONES AS MITICIDES

[75] Inventors: John A. Durden, South Charleston; Anthony A. Sousa, St. Albans, both of W. Va.

[73] Assignee: Union Carbide Corporation, New York, N.Y.

[22] Filed: Aug. 31, 1973

[21] Appl. No.: 393,504

Related U.S. Application Data

[63] Continuation-in-part of Ser. No. 816,024, April 14, 1969, abandoned.

[52] U.S. Cl. ................................ 424/331; 71/115; 71/123; 424/317
[51] Int. Cl.² ......................................... A01N 9/24
[58] Field of Search ................ 71/121, 123, 115; 260/590; 424/331

[56] References Cited
UNITED STATES PATENTS

| | | | |
|---|---|---|---|
| 2,820,738 | 1/1958 | Lityan | 260/590 |
| 3,622,632 | 11/1971 | Holland | 260/590 |

FOREIGN PATENTS OR APPLICATIONS

| | | | |
|---|---|---|---|
| 245,170 | 9/1962 | Australia | 260/590 |

OTHER PUBLICATIONS

Bruynes et al., Recueil Tran. Chim., Vol. 85, 1966, pp. 1259–1263.

*Primary Examiner*—Glennon H. Hollrah
*Attorney, Agent, or Firm*—Robert C. Brown

[57] ABSTRACT

Substituted 2-phenylindan-1,3-diones, especially those in which the 2 and 6 positions of the phenyl ring are substituted, exhibit exceptional miticidal and herbicidal activity.

7 Claims, No Drawings

SUBSTITUTED PHENYL INDANDIONES AS MITICIDES

This application is a continuation-in-part of our co-pending application Ser. No. 816,024, filed Apr. 14, 1969, now abandoned.

This invention relates to methods and compositions for combatting mites, both in their oval and adult stages, and to methods and compositions of controlling undesired vegetation, through the use of certain indandione compounds. In another aspect, the invention relates to certain specifically substituted phenylindandione compounds which are novel per se.

The indandione compounds which are employed as the active ingredients in the miticidal and herbicidal compositions of this invention are 2-phenylindan-1,3-dione compounds responding to the following general formula:

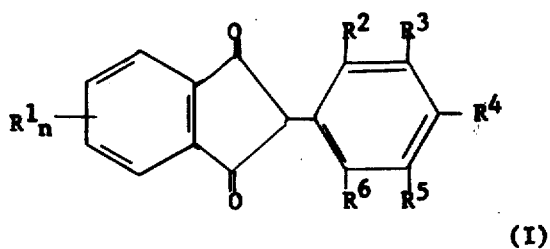

wherein $R^1$ is lower alkyl, preferably not exceeding 4 carbon atoms, lower alkoxy, preferably methoxy, halogen, preferably chlorine or bromine, and $n$ is an integer from 0 to 2; $R^2$ is lower alkyl, preferably methyl, halogen, preferably chlorine or bromine, carboxyl, or trifluoromethyl; $R^3$, $R^4$ and $R^6$ is hydrogen, hydroxy, halogen, preferably chlorine or bromine, lower alkyl and lower alkoxy, preferably methoxy; and $R^5$ is hydrogen, halogen, and lower alkyl, e.g. methyl.

With respect to miticidal applications, compounds in which $R^2$ is lower alkyl, halogen, or trifluoromethyl; $R^3$ is hydrogen or methoxy; $R^4$ is hydrogen, halogen or methyl; $R^5$ is hydrogen; and $R^6$ is hydrogen, halogen, methyl or methoxy, are preferred because of their exceptional activity. Most active are compounds in which both $R^2$ and $R^6$ are small substituent groups, most preferably methyl and chloro, other than hydrogen.

Some of the compounds employed in this invention are known and the others are preparable in analogous fashion (see e.g. Bruynes et al. in *Rec. Trav. Chim.*, 85 11/12, 1259–63, 1966; Netherlands Pat. No. 67/14177 issued Apr. 22, 1968). The following example is illustrative.

EXAMPLE I

Preparation of 4-Methoxy-2-(2′,6′-Dichlorophenyl)indan-1,3-dione

A solution of 2,6-dichlorobenzaldehyde (5.98 grams, 0.034 mole) and 4-methoxyphthalide (5.6 grams, 0.34 mole) in 20.5 milliliters of ethyl acetate was added to a solution of sodium methoxide in methanol (prepared from 2.36 grams of sodium metal and 34 milliliters of methanol). The mixture was then heated under reflux for 1 hour. The bulk of the ethyl acetate and methanol was removed under reduced pressure. The residue was dissolved in water and the solution filtered from insoluble material. Acidification of the filtered alkaline solution afforded 9.0 grams of a yellow solid which was recrystallized from ethanol to give 6.5 grams (59.3%) of the title compound, melting point 163°–165°C. Calc'd: C, 59.83, H, 3.14; Found: C, 59.55, H, 3.19.

The following compounds, representative of those used in this invention, were tested with respect to their miticidal and herbicidal activity.

Suspensions of the test compounds were prepared by dissolving 1 gram of compound in 50 milliliters of acetone in which had been dissolved 0.1 gram (10 per cent of the weight of compound) of an alkylphenoxy polyethoxyethanol surfactant, as an emulsifying or dispersing agent. The resulting solution was mixed into 150 milliliters of water to give roughly 200 milliliters of a suspension containing the compound in finely divided form. The thus-prepared stock suspension contained 0.5 per cent by weight of compound. The test concentrations employed in the tests described hereinbelow were obtained by diluting the stock suspension with water. Serial dilution tests were carried out in the indicated instances to determine the $LD_{50}$ and $LD_{95}$ (concentration of chemical required to kill 50 and 95 per cent, respectively, of the mite population) values for each test compound. The test procedures were as follows:

MITE FOLIAGE SPRAY TEST

Adults and nymphal stages of the two-spotted mite (*Tetranychus urticae* (L.)), reared on Tendergreen bean plants at 80±5°F. and 50±5 per cent relative humidity, were the test organisms. Infested leaves from a stock culture were placed on the primary leaves of two bean plants 6 to 8 inches in height, growing in a 2½ inch clay pot. 150–200 Mites, a sufficient number for testing, transferred from the excised leaves to the fresh plants in a period of 24 hours. Following the 24 hour transfer period, the excised leaves were removed from the infested plants. The test compounds were formulated by diluting the stock suspension with water to give a suspension containing 500 parts of test compound per million parts of final formulation. The potted plants (one pot per compound) were placed on a revolving turntable and sprayed with 100–110 milliliters of test compound formulation by use of a DeVilbiss spray gun set at 40 psig. air pressure. This application, which lasted 30 seconds, was sufficient to wet the plants to run-off. As a control, 100–110 milliliters of a water solution containing acetone and emulsifier in the same concentrations as the test compound formulation, but containing no test compound, were also sprayed on infested plants. The sprayed plants were held at 80±5°F. and 50±5 per cent relative humidity for 6 days, after which a mortality count of motile forms was made. Microscopic examination for motile forms was made on the leaves of the test plants. Any individual which was capable of locomotion upon prodding was considered living. Each compound was then rated according to the following designations:

5 = 80–100% mortality
3 = 40–79% mortality

1 = 0–39% mortality

MITE OVICIDE TEST

The test organism was the egg of the two-spotted mite (*Tetranychus urticae* (L.)), as obtained from adults reared on Tendergreen bean plants under controlled conditions of 80±5°F. and 50±5 per cent relative humidity. Heavily infested leaves from a stock culture were placed on the primary leaves of two bean plants 6 to 8 inches in height, growing in a 2½ inch clay pot. Females were allowed to oviposit for a period of 48 hours and then the leaves of the infested plants were dipped in a solution containing 800 parts of tetraethyl pyrophosphate per million parts of water in order to destroy the reproductory forms and thus prevent further egg laying. This solution of tetraethyl pyrophosphate does not affect the viability of the eggs. The plants were allowed to dry thoroughly. The test compounds were formulated by diluting the stock suspension with water to give a suspension containing 500 parts of test compound per million parts of final formulation. The potted plants (one pot per compound) were placed on a revolving turntable and sprayed with 100–110 milliliters of test compound formulation by use of a DeVilbiss spray gun set at 40 psig. air pressure. This application, which lasted 30 seconds, was sufficient to wet the plants to run-off. As a control, 100–110 milliliters of a water solution containing acetone and emulsifier in the same concentrations as the test compound formulation, but containing no test compound, were also sprayed on plants infested with eggs. The sprayed plants were held at 80±5°F. and 50±5 per cent relative humidity for 6 days, after which a microscopic examination was made of unhatched (dead) and hatched (living) eggs, and each test compound was rated according to the following designations:

5 = 70–100% mortality
3 = 40–69% mortality
1 = 0–39% mortality

PRELIMINARY HERBICIDE SEED GERMINATION TEST

The following seeds are used in this test:
Perennial rye grass — *Solium perenne*
Crabgrass
Red root pigweed — *Amaranthus retroflexus*
Mustard — *Brassica pincea var. foliosa* (Florida broadleaf)

Two seed-soil mixtures are prepared as follows:

| Mixture I | 196 cc. Rye grass seed |
| | 75 cc. Mustard seed |
| | 18,000 cc. sifted, fairly dry soil |
| Mixture II | 99 cc. Crabgrass seed |
| | 33 cc. Amaranthus |
| | 18,000 cc. sifted, fairly dry soil |

Each of above mixtures is rolled separately in 5 gallon containers for approximately ½ hour on ball mill to insure uniform mixing of seeds and soil. For each compound four 3-inch pots are filled with soil to within 1½ inches of top of pots. To 2 of these pots are added 70 cc. of Mixture I. To the remaining 2 pots are added 70 cc of Mixture II. The seed-soil mixture is tamped firmly, and the pots are removed to greenhouse and watered lightly. About 2 hours after planting, 25 milliliters of the test solution are added to each of 2 pots for each soil-seed mixture; i.e., one replicate of each seed mixture per concentration. An equal volume of a water solution containing acetone and an emulsifier in the same concentration as the herbicidal mixture but without the candidate herbicide is also added to each of the soil-seed mixtures. These pots are used as check or control units. The test compounds are formulated by a standard procedure of solution in acetone, addition of an emulsifier, and dilution with water. Preliminary tests are conducted at 1000 ppm. and 100 ppm. The pots are held in the greenhouse and watered lightly until results are taken. Ten to 12 days after application of chemical, injury is noted for each species by comparing treated vs. untreated pots. Ratings are made at both the high and the low concentrations (1000 ppm and 100 ppm) according to the following designations:

5 = no seedlings emerged
4 = few seedlings emerged and/or very severe stunting
3 = moderate reduction in stand and/or moderate stunting
2 = very slight reduction in stand and/or slight stunting
1 = no injury; seedlings appear no different with respect to stand or growth than untreated controls Accordingly, the maximum rating for one test seed species is 10 and the maximum possible total preemergence rating is 40 (10 for each of the four test seed species).

The test data are set forth in the following table:

| Compound No. | Structure (Name) | Miticidal Adult $LD_{50}$ | $LD_{95}$ | Ova $LD_{50}$ | $LD_{95}$ | Herbicidal Total Preemergence |
|---|---|---|---|---|---|---|
| 1 | 2-(2'-methylphenyl)indan-1,3-dione | 200 | >500 | 500 | — | 19 |
| 2 | 2-(2'-ethylphenyl)indan-1,3-dione | — | — | — | — | 18 |
| 3 | 2-(2'-isopropylphenyl)indan-1,3-dione | — | — | — | — | 15 |
| 4 | 2-(2'-t.butylphenyl)indan-1,3-dione | — | — | — | — | 19 |
| 5 | 2-(2'-trifluoromethylphenyl)indan-1,3-dione | 300 | >500 | >500 | — | 23 |
| 6 | 2-(2'-chlorophenyl)indan-1,3-dione | — | — | — | — | 16 |
| 7 | 2-(2'-bromophenyl)indan-1,3-dione | 500 | — | 500 | — | 16 |
| 8 | 2-(2',6'-dimethylphenyl)indan-1,3-dione | 15 | 120 | 25 | 45 | 33 |
| 9 | 2-(2'-methyl-6'-ethylphenyl)indan-1,3-dione | 12 | 300 | 27 | 70 | 35 |
| 10 | 2-(2',6'-diethylphenyl)indan-1,3-dione | 200 | >500 | >500 | — | 33 |
| 11 | 2-(2'-methyl-6'-isopropylphenyl)indan-1,3-dione | >250 | — | >250 | — | — |
| 12 | 2-(2',6'-diisopropylphenyl)indan-1,3-dione | 500 | — | — | — | 31 |
| 13 | 2-(2',3'-dimethoxyphenyl)indan-1,3-dione | — | — | — | — | 19 |
| 14 | 2-(2',4'-dichlorophenyl)indan-1,3-dione | 500 | — | 500 | — | 21 |
| 15 | 2-(2',6'-dichlorophenyl)indan-1,3-dione | 7 | >500 | 20 | 40 | 32 |
| 16 | 2-(2'-bromo-6'-chlorophenyl)indan-1,3-dione | 6 | 500 | 25 | 55 | 29 |
| 17 | 2-(2'-chloro-6'-fluorophenyl)indan-1,3-dione | 35 | 500 | 45 | 120 | 25 |
| 18 | 2-(2'-chloro-6'-methylphenyl)indan-1,3-dione | 10 | 200 | 18 | 50 | 29 |
| 19 | 2-(2',4',6'-trimethylphenyl)indan-1,3-dione | 8 | >500 | 15 | 40 | 38 |
| 20 | 2-(2',4',6'-trimethoxyphenyl)indan-1,3-dione | — | — | — | — | 16 |

-continued

| Compound No. | Structure (Name) | Miticidal Adult LD₅₀ | LD₉₅ | Ova LD₅₀ | LD₉₅ | Herbicidal Total Preemergence |
|---|---|---|---|---|---|---|
| 21 | 2-(2',6'-dimethyl-4'-t.butylphenyl)indan-1,3-dione | — | — | — | — | 17 |
| 22 | 2-(2',6'-dimethyl-4'-methoxyphenyl)indan-1,3-dione | — | — | — | — | 30 |
| 23 | 2-(2',4'-dimethyl-6'-methoxyphenyl)indan-1,3-dione | 15 | >500 | 15 | 50 | 36 |
| 24 | 2-(2',6'-dimethyl-4'-hydroxyphenyl)indan-1,3-dione | — | — | — | — | 29 |
| 25 | 2-(2',4'-dimethyl-6'-hydroxyphenyl)indan-1,3-dione | — | — | — | — | 24 |
| 26 | 2-(2',4',6'-trichlorophenyl)indan-1,3-dione | 15 | >500 | 25 | 120 | 27 |
| 27 | 2-(2',3',6'-trichlorophenyl)indan-1,3-dione | 500 | — | 250 | — | 26 |
| 28 | 2-(2',3',5',6'-tetramethylphenyl)indan-1,3-dione | 500 | — | — | — | 26 |
| 29 | 2-(2',4',6'-trimethyl-3'-methoxyphenyl)indan-1,3-dione | 45 | >500 | 120 | 250 | 24 |
| 30 | 2-(2',4',6'-trimethyl-3'-hydroxyphenyl)indan-1,3-dione | — | — | — | — | 23 |
| 31 | 2-(2',4',6'-trimethyl-3'-chlorophenyl)indan-1,3-dione | — | — | 500 | — | 23 |
| 32 | 2-(2',4',6'-trimethyl-3'-bromophenyl)indan-1,3-dione | — | — | 500 | — | 24 |
| 33 | 2-(2',3',4'-trimethyl-6'-methoxyphenyl)indan-1,3-dione | — | — | — | — | 19 |
| 34 | 2-(2',3',5',6'-tetramethyl-4'-methoxyphenyl)indan-1,3-dione | — | — | — | — | 16 |
| 35 | 2-(2',3',5',6'-tetrachloro-4'-methoxyphenyl)indan-1,3-dione | — | — | — | — | 15 |
| 36 | 2-(2'-carboxyphenyl)indan-1,3-dione | — | — | — | — | 16 |
| 37 | 4-methyl-2-(2',6'-dichlorophenyl)indan 1,3-dione (M.P. 130–132° Calc'd. C, 62.97; H, 3.27 Found C, 62.56; H, 3.50 | 35 | 130 | 25 | 130 | 28 |
| 38 | 5-methyl-2-(2',6'-dichlorophenyl)indan-1,3-dione | 10 | >500 | 40 | 100 | 30 |
| 39 | 4-methoxy-2-(2',6'-dichlorophenyl)indan-1,3-dione | 90 | >500 | 500 | — | 31 |
| 40 | 5-methoxy-2-(2',6'-dichlorophenyl)indan-1,3-dione | 500 | — | — | — | 27 |
| 41 | 4-chloro-2-(2',6'-dichlorophenyl)indan-1,3-dione | — | — | — | — | 20 |
| 42 | 5-chloro-2-(2',6'-dichlorophenyl)indan-1,3-dione | 70 | 500 | 250 | >500 | 24 |
| 43 | 4-bromo-2-(2',6'-dichlorophenyl)indan-1,3-dione | 500 | — | 500 | — | 28 |
| 44 | 4,6-dimethyl-2-(2',6'-dichlorophenyl)indan-1,3-dione | — | — | — | — | 13 |
| 45 | 5,6-dimethyl-2-(2',6'-dichlorophenyl)indan-1,3-dione | — | — | 90 | 260 | 26 |
| 46 | 4-methyl-2-(2',4',6'-trimethylphenyl)indan-1,3-dione | 500 | — | 22 | 60 | 25 |
| 47 | 5-methyl-2-(2',4',6'-trimethylphenyl)indan-1,3-dione | 9 | >500 | 8 | 60 | 37 |
| 48 | 5-t.butyl-2-(2',4',6'-trimethylphenyl)indan-1,3-dione | 65 | >500 | 18 | 100 | 32 |
| 49 | 4-methoxy-2-(2',4',6'-trimethylphenyl)indan-1,3-dione | 25 | >500 | — | 30 | 32 |
| 50 | 5-methoxy-2-(2',4',6'-trimethylphenyl)indan-1,3-dione | 15 | >500 | 50 | 190 | 27 |
| 51 | 4-chloro-2-(2',4',6'-trimethylphenyl)indan-1,3-dione | — | — | — | — | 24 |
| 52 | 5-chloro-2-(2',4',6'-trimethylphenyl)indan-1,3-dione | 75 | >500 | 110 | 250 | 29 |
| 53 | 4-bromo-2-(2',4',6'-trimethylphenyl)indan-1,3-dione | — | — | — | — | 27 |
| 54 | 4,6-dimethyl-2-(2',4',6'-trimethylphenyl)indan-1,3-dione | 40 | >500 | 40 | 100 | 24 |
| 55 | 4,7-dimethyl-2-(2',4',6'-trimethylphenyl)indan-1,3-dione | 500 | — | — | — | 17 |
| 56 | 5,6-dimethyl-2-(2',4',6'-trimethylphenyl)indan-1,3-dione | 500 | — | 60 | 90 | 28 |
| 57 | 4,5-dimethoxy-2-(2',4',6'-trimethylphenyl)indan-1,3-dione | 500 | — | 500 | — | 24 |

It can be seen from the data presented in the above table that structural requirements are more specific for miticidal activity than for herbicidal activity. Generally, the substituent group on the phenyl ring must be small for optimum miticidal activity. Preferably, substitution is at one or both of the 2 and 6 positions with further optional substitution at the 4 position. In addition, the substituent on the benzene nucleus of the indandione structure should be small, e.g. methyl or chloro. Of particularly noteworthy efficacy in miticidal applications are 2-(2',4',6'-trimethylphenyl)indan-1,3-dione (Compound No. 19), 2-(2',6'-dichlorophenyl)indan-1,3-dione (Compound No. 15), and 4-methyl-2-(2',6'-dichlorophenyl)indan-1,3-dione (Compound No. 37). Compound No. 37, which is novel, is particularly outstanding in its steep response curve in a plot of concentration against per cent of kill. The preferred miticides of this invention are effective against phosphate-resistant mites which makes them especially valuable in many applications where conventional miticides fail.

As noted above, herbicidal activity is not as dependent on specific structural characteristics of the compounds used herein as is miticidal activity. Compound 15 is particularly effective against difficult to control weeds such as nut-grass.

The compounds contemplated in this invention may be applied as miticides and herbicides according to methods known to those skilled in the art. Pesticidal compositions containing the compounds as the active toxicant will usually comprise a carrier and/or a diluent, either liquid or solid.

Suitable liquid diluents or carriers include water, petroleum distillates, or other liquid carriers with or without surface active agents. Liquid concentrates may be prepared by dissolving one of these compounds with a non-phytotoxic solvent such as acetone, xylene, or nitrobenzene and dispersing the toxicants in water with the aid of suitable surface active emulsifying and dispersing agents.

The choice of dispersing and emulsifying agents and the amount employed is dictated by the nature of the composition and the ability of the agent to facilitate the dispersion of the toxicant. Generally, it is desirable to use as little of the agent as is possible, consistent with the desired dispersion of the toxicant in the spray so that rain does not re-emulsify the toxicant after it is applied to the plant and wash it off the plant. Nonionic, anionic, or cationic dispersing and emulsifying agents may be employed, for example, the condensation products of alkylene oxides with phenol and organic acids, alkyl aryl sulfonates, complex ether alcohols, quaternary ammonium compounds, and the like.

In the preparation of wettable powder or dust or granulated compositions, the active ingredient is dispersed in and on an appropriately divided solid carrier such as clay, talc, bentonite, diatomaceous earth, fullers earth, and the like. In the formulation of the wettable powders the aforementioned dispersing agents as well as lignosulfonates can be included.

The required amount of the toxicants contemplated her__ __ __ __ applied per acre treated in from 1 to 200 gall__.s __ n_.ore of liquid carrier and/or diluent or in from about 5 to 500 pounds of inert solid carrier and/or diluent. The concentration in the liquid concentrate will usually vary from about 10 to 95 per cent by weight and in the solid formulations from about 0.5 to about 90 per cent by weight. Satisfactory sprays, dusts, or granules for general use contain from about ¼ to 15 pounds of active toxicant per acre.

The pesticides contemplated herein prevent attack by mites upon plants or other material to which the pesticides are applied, and they have high residual toxicity. The toxicants are chemically inert and they are now compatible with substantially any other constituents of the spray schedule, and they may be used in the soil, upon the seeds, or the roots of those plants in which they induce no herbicidal effects.

What is claimed is:

1. A method of controlling mites which comprises applying to the locus thereof a miticidally effective amount of a compound of the formula:

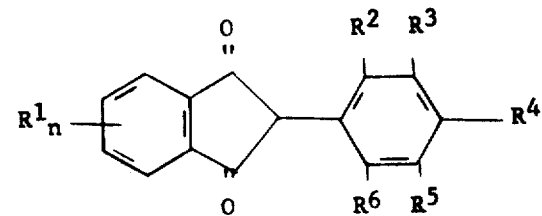

wherein $R^1$ is lower alkyl, lower alkoxy, or halogen, and $n$ is an integer from 0 to 2; $R^2$ is lower alkyl, halogen or trifluoromethyl; $R^3$, $R^4$ and $R^6$ is hydrogen, hydroxy, halogen, lower alkyl and lower alkoxy; and $R^5$ is hydrogen, halogen and lower alkyl.

2. A method of controlling mites in accordance with claim 1 wherein $R^2$ is lower alkyl, halogen, or trifluoromethyl; $R^3$ is hydrogen or methoxy; $R^4$ is hydrogen, halogen or methyl; $R^5$ is hydrogen; and $R^6$ is hydrogen, halogen, methyl or methoxy.

3. A method in accordance with claim 1 wherein $R^2$, $R^4$ and $R^6$ are methyl.

4. A method in accordance with claim 1 wherein $R^2$ and $R^6$ are chlorine.

5. A method in accordance with claim 1 wherein said compound is 2-(2',4',6'-trimethylphenyl)indan-1,3-dione.

6. A method in accordance with claim 1 wherein said compound is 2-(2',6'-dichlorophenyl)indan-1,3-dione.

7. A method in accordance with claim 1 wherein said compound is 4-methyl-2-(2',6'-dichlorophenyl)indan-1,3-dione.

* * * * *